United States Patent [19]

Nick et al.

[11] Patent Number: 5,015,768

[45] Date of Patent: May 14, 1991

[54] 2-((METH)ACRYLAMIDOMETHYL)-1,3-DIKETONES

[75] Inventors: Bernhard Nick, Ludwigshafen; Kaspar Bott, Mannheim; Guenther Schulz, Bad Durkheim, all of Fed. Rep. of Germany

[73] Assignee: BASF Aktiengesellschaft, Ludwigshafen, Fed. Rep. of Germany

[21] Appl. No.: 566,501

[22] Filed: Aug. 13, 1990

Related U.S. Application Data

[62] Division of Ser. No. 360,989, Jun. 2, 1989.

[30] Foreign Application Priority Data

Jun. 8, 1988 [DE] Fed. Rep. of Germany ....... 3819455

[51] Int. Cl.$^5$ .......................................... C07C 231/12
[52] U.S. Cl. .................................... 564/204; 564/207
[58] Field of Search .............................. 564/204, 207

[56]  References Cited

FOREIGN PATENT DOCUMENTS 0188037 7/1986 European Pat. Off. .

Primary Examiner—Richard L. Raymond
Assistant Examiner—P. O'Sullivan
Attorney, Agent, or Firm—Keil & Weinkauf

[57] ABSTRACT

Novel 2-[(meth)acrylamidomethyl]-1,3-diketones have the general formula (I)

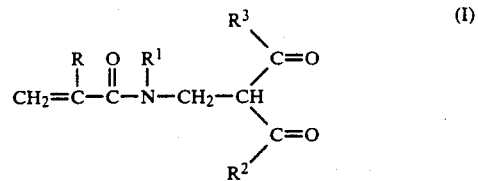

where
R is hydrogen or methyl,
$R^1$ is hydrogen, methyl or ethyl,
$R^2$ and $R^3$ are each alkyl of from 1 to 6 carbon atoms or unsubstituted or substituted aryl of from 6 to 20 carbon atoms, $R^2$ and $R^3$ being identical to or different from each other.

5 Claims, No Drawings

2-((METH)ACRYLAMIDOMETHYL)-1,3-DIKETONES

This is a division of application Ser. No. 360,989, filed June 2, 1989.

The present invention relates to novel 2-[(meth)acrylamidomethyl]-1,3-diketones.

Chelating compounds which form 5- or 6-membered rings with metal cations are common knowledge. A typical example thereof is acetylacetone. Compounds of this type have many possible uses, for example in the isolation or fixation of metals or in preparing firmly adherent protective layers on metal surfaces. There is special interest in chelating compounds having an olefinic double bond capable of free radical polymerization. This is because compounds of this type are suitable for preparing polymers having remarkable properties and many possible uses.

Compounds which contain a chelating 1,3-diketone group and an olefinically unsaturated radical capable of free radical polymerization and which therefore are also referred to as chelating monomers for short are known for example from EP-A-188,037. In these known compounds, the 1,3-diketone group is attached to the (meth)acrylic acid radical via one or two ester functions. Typical examples thereof are

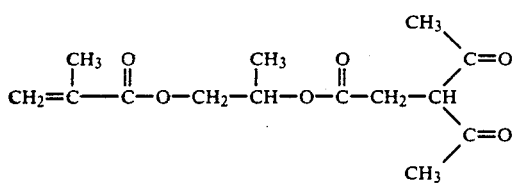

and

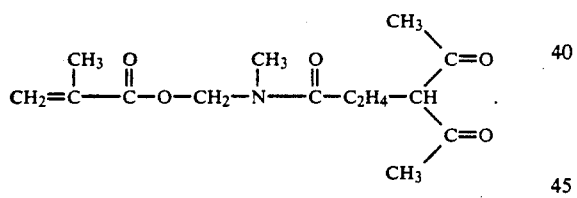

However, these known chelating monomers have the disadvantage that the ester functions they contain are readily saponifiable. This is the reason why these compounds readily decompose in the presence of water, aqueous alkaline solutions, ammonia or amines. They can therefore only be used for purposes where there is no danger of decomposition and hence of loss of the characteristic properties. Moreover, the preparation of the compounds requires several steps to link the 1,3-diketone group to the (meth)acryloyl radical, which further diminishes the attractiveness of these compounds.

It is an object of the present invention to provide stable and simple-to-prepare compounds having a 1,3-diketone group and a radical with an olefinic double bond polymerizable, in particular photopolymerizable, by a free radical mechanism which are free of the prior art disadvantages.

We have found, surprisingly, that this object is achieved by the novel 2-[(meth)acrylamidomethyl]-1,3-diketones of the type specified in more detail hereinafter.

The present invention accordingly provides 2-[(meth)acrylamidomethyl]-1,3-diketones of the general formula (I)

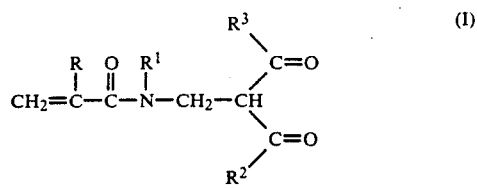

where R, $R^1$, and $R^2$ and $R^3$ are each independently of the others defined as follows:

R as hydrogen or methyl, preferably hydrogen, $R^1$ as hydrogen, methyl or ethyl, preferably hydrogen, $R^2$ and $R^3$ each as alkyl of from 1 to 6 carbon atoms or unsubstituted or for example alkyl-, aryl- or halogen-substituted aryl of from 6 to 20 carbon atoms, $R^2$ and $R^3$ being identical to or different from each other.

Examples of $R^2$ and $R^3$ in the general formula (I) are: methyl, ethyl, n-propyl, i-propyl, n-butyl, sec-butyl, tert-butyl, pent-1-, -2-, or -3-yl and -1-, -2- or -3-yl; phenyl, 2-, 3- and 4-methylphenyl, 2,4 -dimethylphenyl, 4-tert-butyl-, 4-chloro- and 4-bromophenyl, 4-phenylphen-1-yl (biphenylyl), 4-(4'-phenylphen-1'-yl)phen-1-yl (triphenylyl), 1- and 2-naphthyl, phenanthren-7-yl, anthracen-1-yl, fluoren-2-yl and perylen-3-yl. Of these methyl, ethyl, n-propyl and phenyl are preferred according to the invention, with methyl and phenyl being very particularly preferred.

Examples of preferred 2-[(meth)acrylamidomethyl]-1,3-diketones of the general formula (I) according to the invention are

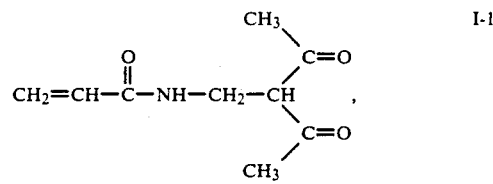

I-1

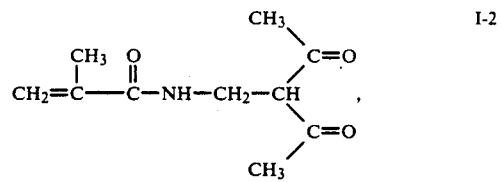

I-2

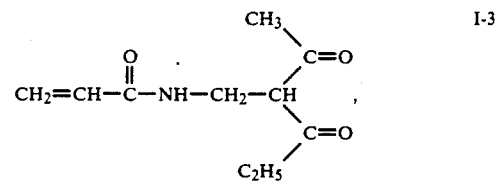

I-3

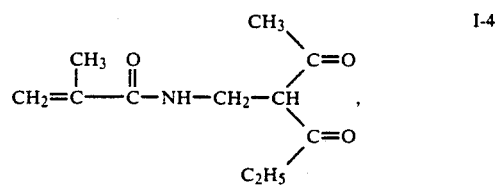

I-4

-continued

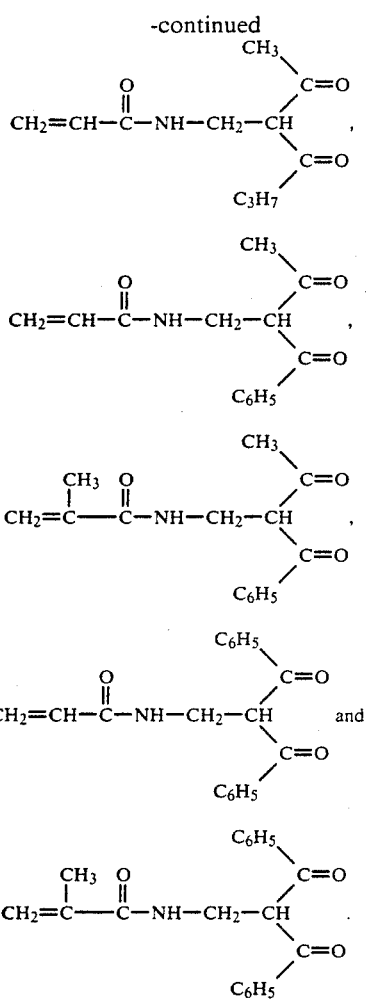

I-5: CH₂=CH—C(O)—NH—CH₂—CH(C(=O)CH₃)(C(=O)C₃H₇)

I-6: CH₂=CH—C(O)—NH—CH₂—CH(C(=O)CH₃)(C(=O)C₆H₅)

I-7: CH₂=C(CH₃)—C(O)—NH—CH₂—CH(C(=O)CH₃)(C(=O)C₆H₅)

I-8: CH₂=CH—C(O)—NH—CH₂—CH(C(=O)C₆H₅)(C(=O)C₆H₅) and

I-9: CH₂=C(CH₃)—C(O)—NH—CH₂—CH(C(=O)C₆H₅)(C(=O)C₆H₅)

Of these, the 2-[(meth)acrylamidomethyl]-1,3-diketones of the formulae I-1 [3-(acrylamidomethyl)-2,4-pentanedione], I-6 [1-phenyl-2-(acrylamidomethyl)-1,3-butanedione] and I-8 [1,3-diphenyl-2-(acrylamidomethyl)-1,3-propanedione] are very particularly preferred.

The 2-[(meth)acrylamidomethyl]-13-diketones of the general formula (I) according to the invention can be prepared by the customary and known methods of preparative organic chemistry. It is of advantage, however, to prepare the 2-[(meth)acrylamidomethyl]-1,3-diketones of the general formula (I) according to the invention in a manner according to the invention by amidomethylation of 1,3-diketones in the presence of strong acids.

This process according to the invention starts from a 1,3-diketone of the general formula (II)

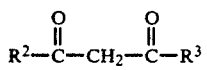

$$R^2-\overset{O}{\underset{\|}{C}}-CH_2-\overset{O}{\underset{\|}{C}}-R^3 \quad (II)$$

where $R^2$ and $R^3$ are identical to or different from each other and are each as defined above in connection with the general formula (I). Examples of $R^2$ and $R^3$ in the general formula (II) are the same as mentioned above for $R^2$ and $R^3$ in the general formula (I). Preferred $R^2$ and $R^3$ are methyl, ethyl, n-propyl and phenyl, in particular methyl and phenyl.

Examples of 1,3-diketones of the general formula (II) which are very particularly preferred for use in the process according to the invention are 2,4-pentanedione (II-1), benzoylacetone (II-2) and 1,3-diphenyl-1,3-propanedione (II-3).

In the process according to the invention, the 1,3-diketones of the general formula (II) are dissolved or dispersed at from −5° to +10° C., in particular at about 0° C., in a sufficient amount of a strong acid as the reaction medium. A suitable amount of acid is in general about 2–20 times the weight of the 1,3-diketone of the general formula (II). Suitable strong acids include inter alia concentrated sulfuric acid, concentrated phosphoric acid and concentrated trifluoromethanesulfonic acid, the first of these being particular advantageous.

To this solution or dispersion of the 1,3-diketone of the general formula (II) is then added an equimolar amount of an N-methylol(meth)acrylamide of the general formula (III)

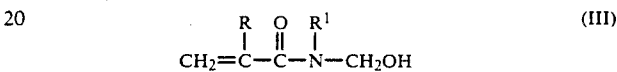

$$CH_2=\overset{R}{\underset{|}{C}}-\overset{O}{\underset{\|}{C}}-\overset{R^1}{\underset{|}{N}}-CH_2OH \quad (III)$$

where R is hydrogen or methyl and, independently thereof, $R^1$ is hydrogen, methyl or ethyl. The preference according to the invention here is given to N-methylol(meth)acrylamides of the general formula (III) where $R^1$ is hydrogen. Very particular preference is given to N-methylolacrylamide. The N-methylol(meth)acrylamides of the general formula (III) can be prepared in a known and simple manner from formaldehyde and the corresponding (meth)acrylamide.

According to the invention, it is of advantage to add to the resulting reaction mixture a customary and known thermal polymerization inhibitor. Suitable polymerization inhibitors are for example trisnonylphenyl phosphite, 2,6-di-tert-butyl-p-cresol, hydroquinone monomethyl ether and polymerized trimethyldihydroquinone, of which hydroquinone monomethyl ether is particularly advantageous. The polymerization inhibitors are in general added to the reaction mixture in an amount of from 0.001 to 5% by weight, based on the N-methylol(meth)acrylamide of the general formula (III).

The resulting reaction mixture of 1,3-diketone of the general formula (II), N-methylol(meth)acrylamide of the general formula (III), strong acid and any polymerization inhibitor, if used, is then stirred at from 15° to 40° C., preferably at from 15° to 30° C., in particular at from 20° to 25° C., for from 1 to 48 hours, preferably from 2 to 40 hours, in particular from 2.5 to 20 hours. During this time, the condensation reaction between the 1,3-diketone of the general formula (II) and the N-methylol(meth)acrylamide of the general formula (III) to give the 2-[(meth)acrylamidomethyl]-1,3-diketones of the general formula (I) according to the invention takes place.

The reacted mixture is then poured onto a quantitatively high excess of, preferably ground, ice, and the 2-[(meth)acrylamidomethyl]-1,3-diketone of the general formula (I) according to the invention precipitates. The precipitated product and any product still present in the aqueous phase are then extracted with an organic solvent, for example toluene, xylene or a halogenated hydrocarbon, such as dichloromethane, and, after the solvent has been evaporated off, recrystallized from suitable solvents or solvent mixtures.

The process according to the invention can be carried out in any desired glass or metal apparatus or plant of the type customary and usual in the field of preparative organic chemistry.

The 2-[(meth)acrylamidomethyl]-1,3-diketones of the general formula (I) according to the invention can be used with particular advantage, owing to their particular advantageous properties, in place of the chelating monomers known from EP-A-188,037 for all the purposes mentioned in said publication. Their superiority over the known chelating monomers rests inter alia on the fact that they are appreciably more stable to hydrolysis than said monomers. Furthermore, the 2-[(meth)acrylamidomethyl]-1,3-diketones of the general formula (I) according to the invention are simpler to prepare than the known chelating monomers, which is why the former are of particular interest for use in industry. The 2-[(meth)acrylamidomethyl]-1,3-diketones of the general formula (I) according to the invention can be used with advantage as convenient synthetic intermediates for the preparation of polymerizable metal chelate complexes or of polymers capable of metal chelation. Or they can be used as photopolymerizable monomers in light-sensitive recording materials. These light-sensitive recording materials, which are customarily used for the production of relief, letterpress, flexographic, intaglio or offset printing plates or else of image structured resist layers, have particular unexpected advantages owing to the presence of 2-[(meth)acrylamidomethyl]-1,3-diketones of the general formula (I). The use of the 2-[(meth)acrylamidomethyl]-1,3-diketones of the general formula (I) according to the invention as intermediates for the preparation of polymerizable heterocyclic compounds is also very favorable. To this end, the 2-[(meth)acrylamidomethyl]-1,3-diketones of the general formula (I) according to the invention are reacted for example with hydroxylamine, hydroxylamine derivatives, hydrazine or hydrazine derivatives in a simple manner to give (meth)acrylamidomethyl-containing isoxazoles or pyrazoles in high yields. There is no danger here of the link between the 1,3-diketone group or the heterocyclic group and the (meth)acryloyl radical capable of free radical polymerization being broken by undesirable side reactions.

Examples

EXAMPLE 1

Preparation and characterization of 3-(acrylamidomethyl)-2,4-pentanedione

To 500 ml of concentrated sulfuric acid were added in succession at 0° C. 1.0 g of hydroquinone monomethyl ether, 64.5 g of 2,4-pentanedione and 64.8 g of N-methylolacrylamide. The reaction mixture was then stirred at 20° C. for 4 hours to ensure complete conversion and was then poured onto 2 kg of ground ice. The resulting precipitate of 3-(acrylamidomethyl)-2,4-pentanedione was dissolved in dichloromethane, and the resulting solution was separated from the aqueous phase. The solvent was then evaporated, and the resulting product was recrystallized from toluene.

60.3 g of crude 3-(acrylamidomethyl)-2,4-pentanedione were obtained, corresponding to a yield of 51% by weight, based on the starting materials. The product obtained had a melting point of 108°-110° C. The elemental composition of the product in % by weight was determined by means of customary and known chemical analysis as:

| Elemental analysis: | C 59.0 | H 7.0 | O 26.3 | N 7.7 |
| --- | --- | --- | --- | --- |
| Theory: | C 59.0 | H 7.16 | O 26.2 | N 7.65 |

The $^1$H-NMR and IR spectroscopy measurements confirmed the presence of the desired compound.

EXAMPLE 2

Preparation and characterization of 1-phenyl-2-(acrylamidomethyl)-1,3-butanedione Example 1 was repeated to prepare 1-phenyl-2-(acrylamidomethyl)-1,3-butanedione from 100 g of benzoylacetone and 64.8 g of N-methylolacrylamide.

Recrystallization of the product from a mixture of 3 parts by volume of cyclohexane and 1 part by volume of ethanol gave 105 g of 1-phenyl-2-(acrylamidomethyl)-1,3-butanedione, corresponding to a pure yield of 70% by weight. The product had a melting point of 125°-126° C.

| Elemental analysis: | C 68.7 | H 6.0 | O 19.7 | N 5.7 |
| --- | --- | --- | --- | --- |
| Theory: | C 68.56 | H 6.16 | O 19.57 | N 5.71 |

The $^1$H-NMR and IR spectroscopy measurements confirmed the presence of the desired compound.

EXAMPLE 3

Preparation and characterization of 1,3-diphenyl-2-(acrylamidomethyl)-1,3-propanedione Example 1 was repeated to prepare 1,3-diphenyl-2-(acrylamidomethyl)-1,3-propanedione from 143 g of 1,3-diphenyl-1,3-propanedione and 64.8 g of N-methylolacrylamide.

Recrystallization of the product from methanol gave 127 g of 1,3-diphenyl-2-(acrylamidomethyl)-1,3-propanedione, corresponding to a pure yield of 65% by weight. The product had a melting point of 146°-148° C.

| Elemental analysis | C 74.1 | H 5.6 | O 15.8 | N 4.5 |
| --- | --- | --- | --- | --- |
| Theory: | C 74.25 | H 5.58 | O 15.62 | N 4.56 |

The $^1$H-NMR and IR spectroscopy measurements confirmed the presence of the desired compound.

EXAMPLES 4 to 7

Use of 2-[(meth)acrylamidomethyl]-1,3-diketones according to the invention as intermediates for preparing heterocycles which are polymerizable by a free radical mechanism

EXAMPLE 4

3-Phenyl-4-(acrylamidomethyl)-5-methylisoxazole

A mixture of 34.6 g of the 1-phenyl-2-(acrylamidomethyl)-1,3-butanedione prepared as described in Example 2, 9.84 g of hydroxylammonium chloride, 11.6 g of sodium acetate, 180 ml of acetic acid and 180 ml of water was refluxed for 5 minutes, cooled down to room temperature, and diluted with 600 ml of water. The resulting crystalline precipitate was filtered off with suction and washed with diethyl ether. This gave 27.0 g of 3-phenyl-4-(acrylamidomethyl)-5-methylisoxazole, corresponding to a yield of 79% by weight. The product had a melting point of 149°-151° C.

| Elemental analysis | C 69.4 | H 5.9 | O 13.1 | N 11.6 |
|---|---|---|---|---|
| Theory | C 69.41 | H 5.82 | O 13.21 | N 11.56 |

The $^1$H-NMR and IR spectroscopy measurements confirmed the presence of the desired compound.

EXAMPLE 5

3-Phenyl-4-(acrylamidomethyl)-5-methylpyrazole

A mixture of 29.4 g of the 1-phenyl-2-(acrylamidomethyl)-1,3-butanedione prepared as described in Example 2, 15.6 g of hydrazinium hydrogen sulfate, 19.7 g of sodium acetate, 180 ml of acetic acid and 180 ml of water was refluxed for 5 minutes, cooled down to room temperature, and diluted with 600 ml of water. The resulting crystalline precipitate was filtered off with suction and washed with diethyl ether. This gave 23.1 g of 3-phenyl-4-(acrylamidomethyl)-5-methylpyrazole, corresponding to a yield of 80%. The product had a melting point of 191°–193° C.

| Elemental analysis | C 69.4 | H 6.3 | N 17.2 |
|---|---|---|---|
| Theory: | C 69.69 | H 6.27 | N 17.41 |

The $^1$H-NMR and IR spectroscopy measurements confirmed the presence of the desired compound

EXAMPLE 6

1,3,5-Triphenyl-4-(acrylamidomethyl) pyrazole

A mixture of 67.4 g of the 1,3-diphenyl-2-(acrylamidomethyl)- 1,3-diphenyl-2-(acrylamidomethyl)-1,3-propanedione prepared as described in Example 3, 23.8 g of phenylhydrazine, 230 ml of acetic acid and 50 ml of water was heated at 90° C. for 6 minutes. On cooling down to room temperature, a product crystallized out (58.2 g) and was recrystallized from ethanol.

The recrystallized product had a melting point of 189°–191° C. The $^1$H-NMR measurement confirmed the presence of 1,3,5-triphenyl-4-(acrylamidomethyl)-pyrazole:

$^1$H-NMR (dimethyl sulfoxide; 300 MHz): δ=4.20 (doublet, 2H, —CH$_2$—), δ=5.60 (doublet, 1H, H—C=C), δ=6.15 (doublet, 1H, H—C=C), δ=6.30 (doubled doublet, 1H, H—C=C), δ=7.2–7.8 (multiplet, 15H, aromatic H), δ=8.60 (triplet, 1H, NH).

EXAMPLE 7

1,5-Diphenyl-3-methyl-4-(acrylamidomethyl)pyrazole

A mixture of 29.4 g of the 1-phenyl-2-(acrylamidomethyl)-1,3-butanedione prepared as described in Example 2, 12.9 g of phenylhydrazine, 180 ml of acetic acid and 180 ml of water was refluxed for 5 minutes, cooled down to room temperature, and diluted with 600 ml of water. The resulting crystalline precipitate was filtered off with suction and washed with diethyl ether. This gave 37.4 g of 1,5-diphenyl-3-methyl-4-(acrylamidomethyl)pyrazole having a melting point of 157°–159° C.

$^1$H-NMR spectroscopy confirmed the presence of this product:

$^1$H-NMR (dimethyl sulfoxide; 300 MHz): δ=2.25 (singlet, 3H, CH$_3$), δ=4.12 (doublet, 2H, —CH$_2$—), δ=5.60 (doublet, 1H, H—C=C), δ=6.12 (doublet, 1H, H—C=C), δ=6.25 (doubled doublet, 1H, H—C=C), δ=7.10–7.45 (multiplet, 10H, aromatic H), δ=8.30 (triplet, 1H, NH).

We claim:

1. The process for preparing a 2-[(meth)acrylamidomethyl]-1,3-diketone, which comprises condensing a 1,3-diketone of the formula (II)

$$R^2-\underset{\underset{O}{\|}}{C}-CH_2-\underset{\underset{O}{\|}}{C}-R^3 \quad (II)$$

where $R^2$ and $R^3$ are identical to or different from each other and each is alkyl of from 1 to 6 carbon atoms or unsubstituted aryl of from 6 to 20 carbon atoms or a phenyl radical substituted by one halogen radical or one phenyl radical or one or two alkyl radicals, with an N-methylol(meth)acrylamide of the formula (III)

$$CH_2=\underset{\underset{R}{|}}{C}-\underset{\underset{O}{\|}}{C}-\underset{\underset{R^1}{|}}{N}-CH_2OH \quad (III)$$

where R is hydrogen or methyl and $R^1$ is hydrogen, methyl or ethyl, in a strong acid as the reaction medium to obtain a 2-[(meth)acrylamidomethyl]-1,3-diketone of the formula (I)

$$CH_2=\underset{\underset{R}{|}}{C}-\underset{\underset{O}{\|}}{C}-\underset{\underset{R^1}{|}}{N}-CH_2-CH\underset{\diagdown C=O}{\overset{\diagup C=O}{\phantom{x}}}\quad (I)$$

(with $R^3$ on upper C=O and $R^2$ on lower C=O)

where R, $R^1$, $R^2$ and $R^3$ are each independently of the others defined as follows:

R is hydrogen or methyl, $R^1$ is hydrogen, methyl or ethyl $R^2$ and $R^3$ each is alkyl of from 1 to 6 carbon atoms or unsubstituted aryl of from 6 to 20 carbon atoms or a phenyl radical substituted by one halogen radical or one phenyl radical or one or two alkyl radicals, $R^2$ and $R^3$ being identical to or different from each other.

2. A process as claimed in claim 1, wherein R and $R^1$ in the formula (III) are each hydrogen and $R^2$ and $R^3$ in the formula (II) are each methyl or phenyl.

3. A process as claimed in claim 1, wherein the strong acid used as the reaction medium is sulfuric acid, trifluoromethanesulfonic acid or phosphoric acid.

4. A process as claimed in claim 3, wherein the reaction medium used is concentrated sulfuric acid.

5. A process as claimed in claim 1, wherein the condensation reaction is carried out in the presence of a thermal polymerization inhibitor.

* * * * *